United States Patent [19]

Imran et al.

[11] Patent Number: 5,349,964
[45] Date of Patent: Sep. 27, 1994

[54] DEVICE HAVING AN ELECTRICALLY ACTUATABLE SECTION WITH A PORTION HAVING A CURRENT SHUNT AND METHOD

[75] Inventors: Mir A. Imran, Palo Alto; Gholam-Reza Zadno-Azizi, Newark; Mark L. Pomeranz, Los Gatos, all of Calif.

[73] Assignee: Intelliwire, Inc., Sunnyvale, Calif.

[21] Appl. No.: 57,098

[22] Filed: May 5, 1993

[51] Int. Cl.$^5$ ............................................. A61B 5/00
[52] U.S. Cl. ................................. 128/772; 128/657; 604/95; 604/281
[58] Field of Search ............... 128/657, 772; 604/95, 604/281

[56] References Cited

U.S. PATENT DOCUMENTS

| | | | |
|---|---|---|---|
| 4,881,981 | 11/1989 | Thoma et al. | 148/11.5 R |
| 5,055,101 | 10/1991 | McCoy | 128/657 |
| 5,143,085 | 9/1992 | Wilson | 128/657 |
| 5,188,111 | 2/1993 | Yates et al. | 128/657 |

Primary Examiner—Max Hindenburg
Attorney, Agent, or Firm—Flehr, Hohbach, Test, Albritton & Herbert

[57] ABSTRACT

Device comprising an elongate tubular member having proximal and distal extremities and having a section with a plurality of lumens extending from the proximal extremity to the section. At least two conductive elements are disposed in the lumens in said section of the elongate tubular member. The conductive elements are formed of a conductive metal alloy having a recoverable strain in excess of 1% and exhibiting a martensitic phase transformation. Electrical current is supplied to the at least one conductive element. The section has at least one portion. A current conductor is carried by said at least one conductive element for shunting current flow around the at least one portion of said at least one conductive element.

27 Claims, 2 Drawing Sheets

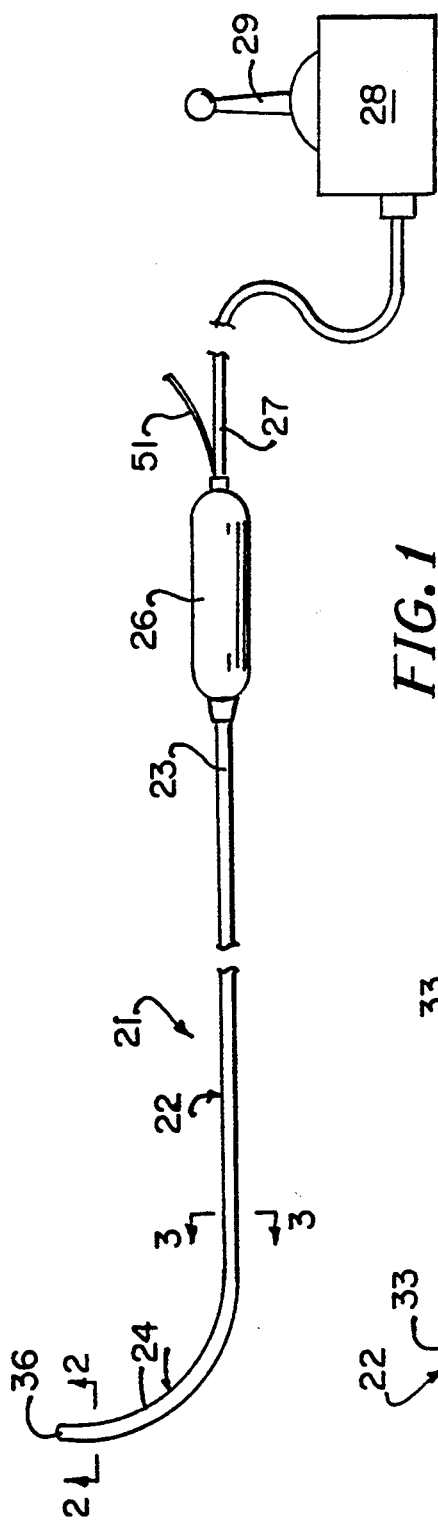
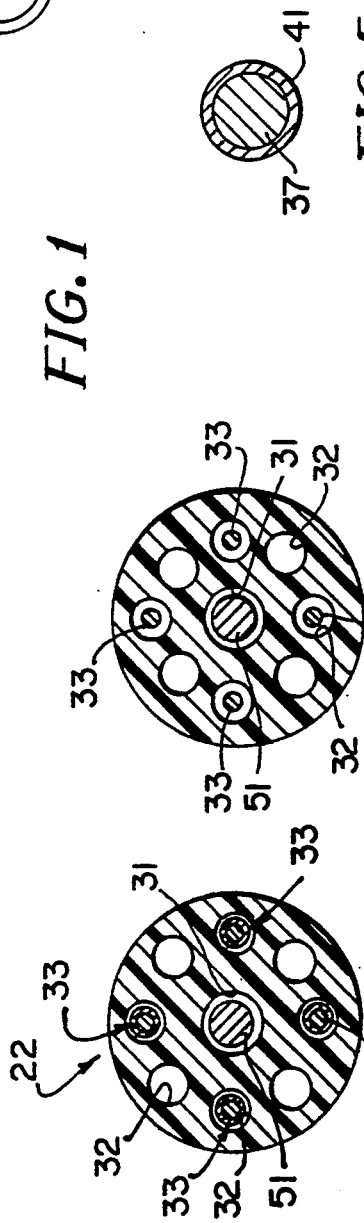
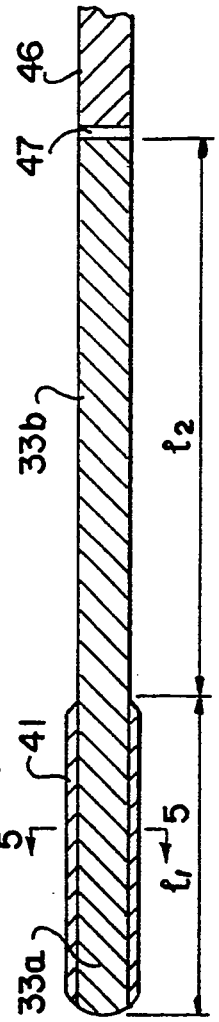

DEVICE HAVING AN ELECTRICALLY ACTUATABLE SECTION WITH A PORTION HAVING A CURRENT SHUNT AND METHOD

This invention relates to a device having an electrically actuatable section with one or more portions having a current shunt and a method.

Heretofore flexible elongate devices such as steerable catheter and guide wires have been provided. At least some of these devices typically have been formed of a plastic material with the distal extremity, as for example the last four inches, being formed of a very soft plastic material and in which there have been disposed conductive elements. The conductive elements when heated to cause steering also heat the plastic so it becomes softer and compresses and takes a set corresponding to the bend created by the steering so that when energy was removed from the conductor, the distal extremity would retain this set and would not come back to a normally straight position. This was found to be very undesirable because this would thereafter definitely limit the maneuverability of the distal extremity of the flexible elongate device. There is therefore need for a new and improved flexible elongate device which will overcome this problem.

In general, it is an object of the present invention to provide a device having an electrically actuatable section which will return to a normal position after having a portion thereof has been moved into a desired location.

Another object of the invention is to provide a device and method in which the heat generated at the section of the flexible elongate device is substantially reduced.

Another object of the invention is to provide a device and method of the above character in which movement in the section can be made to occur in predetermined spaced-apart locations.

Another object of the invention is to provide a device and method of the above character in which complex bends can be accomplished.

Another object of the invention is to provide a flexible elongate device and method of the above character in which preprogrammed shapes can be provided.

Additional objects and features of the invention will appear from the following description in which the preferred embodiments are set forth in detail in conjunction with the accompanying drawings.

FIG. 1 is a side elevational view of a flexible elongate device incorporating the present invention being used with a controller.

FIG. 2 is a cross-sectional view taken along the line 2—2 of FIG. 1.

FIG. 3 is a cross-sectional view taken along the line 3—3 of FIG. 1.

FIG. 4 is an enlarged detail view of the proximal extremity of one of the conducting elements utilized in the device shown in FIG. 1 with a conductive plating carried thereby.

FIG. 5 is a cross-sectional view taken along the line 5—5 of FIG. 4.

Figure 6:
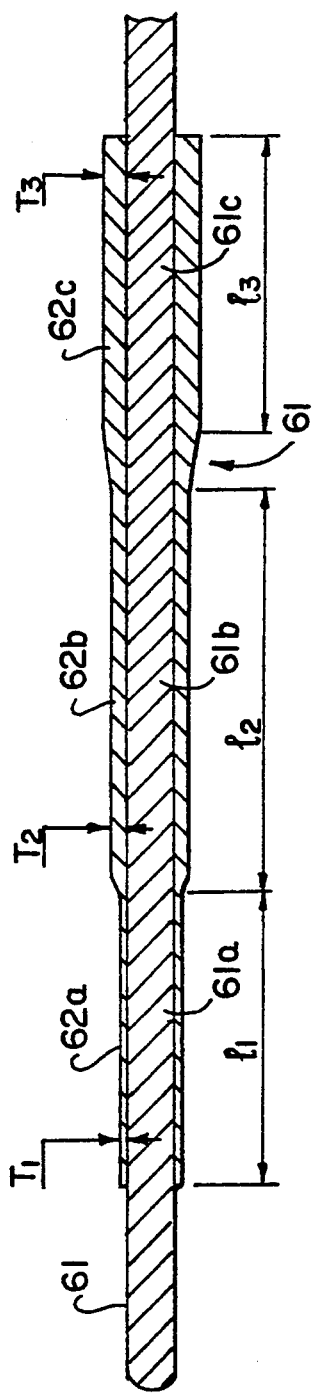
FIG. 6 is a cross-sectional view of a conductive element having a stepped conductive plating carried thereby.

In general, the device incorporating the present invention is comprised of an elongate tubular member having proximal and distal extremities and a section thereof having a plurality of lumens and extending therethrough from the proximal extremity to the section. At least two conductive elements are disposed in the lumens in the section of the tubular member. At least one of the elements is formed of a conductive metal alloy having a recoverable strain in excess of 1% and exhibits a martensitic phase transformation. Means is coupled to the conductive elements for selectively applying electrical current to at least one conductive element to cause selective heating of the same. Conductive means is carried by the conductive element for shunting current by reducing the resistivity of the conductive elements along a certain portion thereof.

More in particular as shown in the drawings, the device 21 consists of a flexible elongate tubular member 22 having proximal and distal extremities 23 and 24. The proximal extremity 23 is secured to a handle 26 which is connected to a cable 27 that is connected to a controller 28. The controller 28 is provided with a joy stick control 29. The device 21 thus far described can be generally of the type described in co-pending application, Ser. No. 07/793,858 filed on Nov. 18, 1991 now U.S. Pat. No. 5,238,005 in which the distal extremity can be steered in directions as determined by the position of the joy stick control 29.

As described in said co-pending application, Ser. No. 07/793,858 filed on Nov. 18, 1991, now U.S. Pat. No. 5,238,005 the flexible elongate tubular member 22 is provided with a central lumen 31 and a plurality of circumferentially spaced-apart lumens 32 surrounding the central lumen 31 and extending from the proximal extremity to the distal extremity of the flexible elongate tubular member 22. The flexible elongate tubular member 22 can be formed of a suitable material such as plastic and can have a suitable size, as for example four or eight French which corresponds to a diameter ranging from 0.054 inches to 0.104 inches. The lumens 32 can have a diameter ranging from 0.003 to 0.015 inches.

A plurality of conductive elements 33 are disposed in the lumens 32. Typically to accomplish steering, at least three of such conductive elements 33 are provided which are circumferentially spaced-apart in the lumens 32. The conductive elements can have a suitable size, as for example 0.005 inches. The distal extremities of the conductive elements 33 can be connected together electrically at the tip 36 of the flexible elongate tubular member 22 to a return conductor 37 disposed in another of the lumens 32.

The conductive elements 33 can be formed of a material which has a recoverable strain in excess of 1.0%. Such characteristics can be provided by certain metal alloys which are typically called shape-memory alloys which exhibit martensitic phase transformations. Such alloys include those which exhibit non-linear superelasticity (typically Ni-Ti with Ni at 49–51.5% atomic) and those which exhibit linear superelasticity (typically Ni-Ti in near equi-atomic composition which have been cold worked). Both the non-linear and linear superelastic alloys return to their shapes when the stress is removed. The shape-memory alloys also include alloys which return to their initial shape when they are thermally activated by increasing the temperature to which they are subjected above the martensitic phase transformation for the alloy. Included in these thermally activated shape-memory alloys are those which exhibit a wide hysteresis of approximately 20° C. and larger. Such alloys can be stored while in the martensitic state and heated one time to transport to austenite. Cooling to the same starting temperature does not cause a reverse transformation to occur because of the wide hysteresis. The composition and behavior of the shape-memory alloys are discussed in a book entitled "Engineering Aspects of Shape-Memory Alloys" published in 1990 by Butterworth-Heinemann, Ltd. of London and Boston.

The present invention is particularly interested in those alloys which are thermally actuated. Products made of thermally actuated shape-memory alloys such as Ni-Ti binaries and Ni-Ti ternaries require a heat source to transform from the low temperature soft martensitic phase into the high temperature hard austenitic phase. This is obtained, in most applications, through passing an electrical current through the material or by other means such as various techniques of convection heating or simply the use of heat from the body, as for example from the human body. Thus for this purpose, a commercially available shape-memory wire such as Nitinol has been selected. It can be circular in cross section as shown. In the case of a straight shape-memory wire, the thermomechanical treatment and cross-sectional area are constant across the entire length the martensitic phase transformation will occur simultaneously at all locations when the transformation temperature is reached. This will result in simultaneous shape and stiffness changes throughout the wire. In many applications, however, it is desirable to have either various stiffnesses in the same part or to have shape recoveries that do not occur simultaneously.

In accordance with the present invention, at least one portion of the conducting element is provided with means for shunting current around one or more portions of the conductive element to thereby reduce the resistivity of that portion or portions of the conductive elements 33. This portion has been designated as the length L1 in FIG. 4 which, in connection with the present invention, can be of a suitable length, as for example 3–6 inches and preferably approximately 4 inches in length. In order to reduce the resistivity of this portion so that electrical current will be shunted and will not flow through that portion of the conductive element, plating 41 is provided which extends over the length of this portion and is formed of a material which has a substantially higher conductivity than that of the element so that current flowing through the conductive element will have a propensity to flow through the plating rather than through the conductive element. It has been found desirable to utilize a material which is highly conductive such as the noble metals such as gold and silver. However, it is possible to use lesser conductive metals, as for example copper for this purpose.

The plating can be applied by standard electroplating processes. Thus by way of example, the portion or portions to be plated can be striped with an acid etch to remove any undesirable oxides and other foreign materials in which electroplating can be accomplished by dipping the portions to be plated in electrolyte bath to provide a plating of the desired thickness, as for example from 50 to 300 microinches. The following equation can be used to determine the plating thickness required to reduce the overall resistance by a factor of n:

$$\text{Thickness (plating)} = r\left(\sqrt{\frac{n \cdot \rho_{Au\ or\ Ag}}{\rho_{Ni-Ti}} + 1} - 1\right) \tag{1}$$

where
- $r$ = radius of bare Ni-Ti wire
- $n$ = desired ratio in resistance for the plated part, e.g., $n=5$ means the plated part is 5 times less resistant.
- $\rho_{(Ni-Ti)} \approx 6.67 \times 10^{-7}$ $\Omega$-m
- $\rho_{(Au)} \approx 2.44 \times 10^{-8}$ $\Omega$-m
- $\rho_{(Ag)} \approx 1.65 \times 10^{-8}$ $\Omega$-m After the plating has been electrolytically deposited, adhesion to the conductive elements 33 can be assured by annealing the distal extremities at a suitable temperature 100° to 300° C. for a period of time ranging from 10 min. to 2 hrs. By utilizing this plating 41, it is possible to reduce the resistivity of that portion of the conductive element thereby and reducing the I$^2$R heating. By providing such plating it is ensured that the Nitinol material forming the conductive element 33 will not be heated to a temperature to cause a martensitic phase transformation. Thus, that portion can be caused to remain in the martensitic state and not be transformed out of the martensitic state.

In order to obtain the desired shrinkage of the conductive elements 33 to accomplish steering of the distal extremity, it has been necessary to provide an additional portion 33b with the length L2 in FIG. 4 which typically can have a length from 4 to 5 inches which extends into the stiffer portion of the flexible elongate tubular member 22 proximally of the portion 33a. This portion 33b is of the same cross-sectional area as the portion 33a. The proximal extremity of each of the conductive elements 33 is connected to an electrical conductor, as for example one of copper which is bonded to the conductive 33 by a weld, solder or crimp joint 47. The electrical conductors 46 extend to the proximal extremity 23 of the flexible elongate tubular member 22 and are connected into the handle 26 and to the controller 28 so that electrical energy can be supplied to the conductors 46 selectively in accordance with the positioning of the controller handle 29. The return conductor 37 is also brought back to the handle 26 and the controller 27 so that a circuit can be completed for supplying electrical energy through the conductive elements 33.

The central lumen 31 which is provided in the flexible elongate tubular member 22 can be used for various purposes, as for example in accordance with the present invention, a stiffening wire formed of a suitable material such as stainless steel can be disposed in the central lumen 31. By way of example the lumen 31 could have a suitable diameter such as 0.040 inches and the stiffening wire therein could have a diameter of 0.020 inches or greater. The stiffening wire can extend the length of the flexible elongate tubular member 22 and can extend out of the operating handle 26 so that it can be controlled in position by moving the same longitudinally in the lumen 31. By utilizing such a stiffening wire it is possible to adjust the bend location for the distal extremity of the flexible elongate tubular member. Alternatively, it should be appreciated that the stiffening wire 51 can extend the entire length of the flexible elongate tubular member 22 and have the desired taper at the distal extremity and be connected permanently into the distal extremity so that it can serve as a return conductor in place of the return conductor 37.

Operation and use of the device 21 shown in FIG. 1 may now be briefly described as follows. Also, let it be assumed that the device is to be utilized in a medical procedure such as that described in co-pending application Ser. No. 07/793,858 filed on Nov. 18, 1991 now U.S. Pat. No. 5,238,005. Let it be assumed that the device has been introduced into the femoral artery of a patient and that the distal extremity has been advanced toward the heart of the patient and it is desired to enter one of the vessels supplying blood to the heart. While visualizing the same under fluoroscopy, the distal extremity can then be steered by operation of the joy stick 29. Electrical energy is supplied to the appropriate conductive elements 33 causing the portions 33b to heat and to shrink to cause bending of the distal extremity by pulling forces being applied to the portion 33a to cause the distal extremity 24 of the flexible elongate tubular member to bend in the desired direction. This bending can be accomplished without heating the soft plastic section of the flexible elongate tubular member 22. This occurs because the electrical energy supplied through the conductive element 33 will be shunted by and pass through the plating 41 which has a much lower resistivity than the conductive element and thus provides much less $I^2R$ heating so that the plastic in the flexible elongate tubular member 22 will not become soft and take a permanent set and thus will not inhibit or prevent return of the flexible elongate tubular member 22 to its original normal state, as for example a straight state.

The distal extremities of the conductive elements 33 can be readily visualized under x-ray because of the material forming the conductive elements 33 as well as the plating 41 provided thereon. However, it should be appreciated that if additional radiopacity is desired bands of a more radiopaque material such as platinum tungsten alloys and palladium bands can be provided in longitudinally spaced-apart increments on the distal extremity of the flexible elongate tubular member 22. The increased radiopacity can also be achieved by loading the plastic used to create the flexible elongate tubular member 22 with a radiopaque material such as bismuth subcarbonate or barium sulfate.

Thus it can be seen by shunting the current flow around the portions 33a of the conductive elements 33 it is possible to have those portions remain in their martensitic state and to also greatly reduce the $I^2R$ heating which is produced by passing electrical energy through the conductive elements 33 to cause the selective bending of the distal extremity of the flexible elongate member 22 and thereby avoiding softening of the plastic and preventing the plastic from taking on a permanent set which would inhibit or restrain the movement of the distal extremity of the flexible elongate tubular member 22 to its normal or home position.

Figure 7:
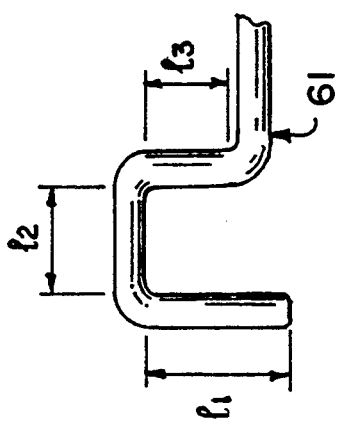
FIG. 7 shows the preformed shape which can be obtained by the construction shown in FIG. 6.

In connection with the present invention it should be appreciated that by selective plating of the conductive elements which are utilized for steering that different bending characteristics as well as different types of bends can be achieved in a section of the flexible elongate tubular member, as for example in the distal extremity of the flexible elongate tubular member 22. Thus by way of example as shown in FIG. 6, there has been provided a conductive element 61 also formed of a material exhibiting shape-memory such as Nitinol which is provided with three different portions 61a, 61b and 61c. The portions 61a, 61b and 61c can be of various lengths, as for example they can be each of two inches in length. These portions 61a, 61b and 61c have been provided with a conductive coating or plating 62 having three zones 62a, 62b and 62c corresponding to the portions 61a, 61b and 61c of the conductive element which by way of example have three different thicknesses with the zone 62a having the least thickness, 62b having intermediate thickness and 62c having the greatest thickness. By way of example, the zone 62a can have a thickness of 100 microinches, 62b a thickness of 200 microinches and zone 62c a thickness of 300 microinches. With such a construction it can be seen that when a current is passed through the conductive element 61, more current will flow through the portion 61a because of the thinner plating 62a and progressively less current will flow through the portions 61b and 61c because of the thicker platings 62a and 62c provided which will shunt more of the current through the plating. As the current is increased that passes through the conductive element 61, the current will be great enough at some value in the portion 61a to cause sufficient heating to cause a martensitic transformation into austenite to occur in the portion 61a to cause it to shrink or contract or to change shape. A further increase in the current flow at some point will cause sufficient heating in the portion 61b exceed the martensitic transformation point and also cause it to shrink or change shape. A still further increase in current will cause a similar heating in the portion 61c to cause the martensitic transformation to occur in that portion 61c to cause further shrinking or change in shape. In this manner it can be seen that by appropriate plating, preprogrammed shapes can be provided in a section, as for example the distal extremity of a flexible elongate tubular member 22. Thus by merely increasing the current levels it is possible to achieve different shapes in the distal extremity of the conductive element, as for example as shown in FIG. 7.

Figure 8:
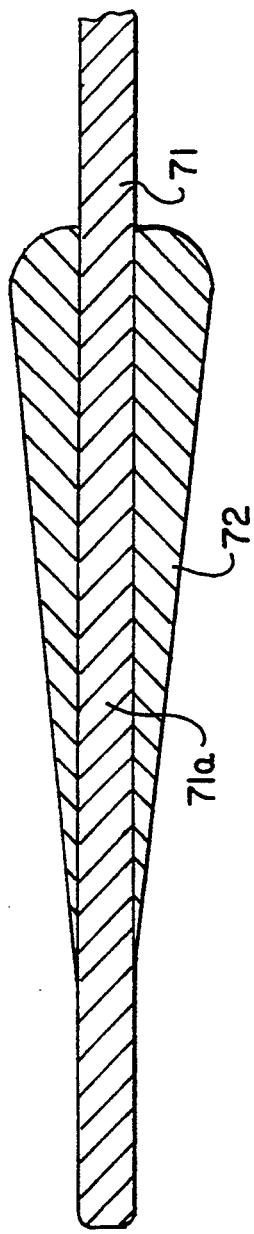
FIG. 8 is a cross-sectional view of another conductive element incorporating the present invention in which a tapered coating is provided on the distal extremity of the conductive element.

Another embodiment of the present invention is shown in FIG. 8 in which a conductive element 71 formed of the same material hereinbefore described is provided in which a plating 72 has been provided on one portion 71a of the conductive element 71. The plating 72 as shown has a tapered thickness which can range from 0 microinches to as much as 300 or 400 microinches at its thickest portion. With such a plating, current passing through the portion 71a of the conductive element 71 would largely be shunted past the conductive element into the plating 72 at the thickest portion with decreasing amounts of current going through the plating. The thickness of the plating decreases to cause a greater current flow through the conductive element 71 and therefore greater $I^2R$ heating of the conductive element to cause progressive transformation of the conductive element from a martensitic state to an austenitic state in direction from left to right as viewed in FIG. 8. Thus it can be seen that by providing different tapers in the plating, different configurations for the bending in the distal extremity of the flexible elongate tubular member 22 can be achieved.

Figure 9:
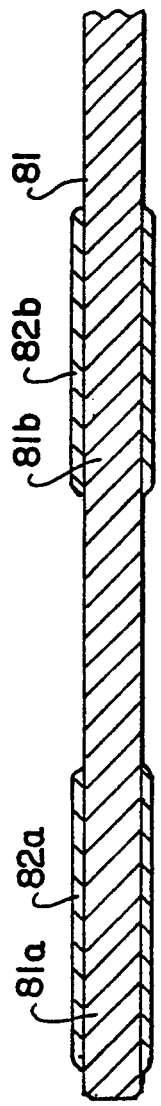
FIG. 9 is a cross-sectional view of another embodiment of a conductive element incorporating the present invention in which the plating is provided on spaced-apart positions on the conductive element.

Also in accordance with the present invention, it should be appreciated that the plating which is utilized for shunting current around the conductive element can be provided on longitudinally spaced-apart portions in a section of the flexible elongate tubular member to achieve still different shapes in the bends in that section, as for example in the distal extremity of the flexible elongate tubular member 22. Thus as shown in FIG. 9 there has been provided a conductive element 81 having spaced-apart portions 81a and 81b which is provided with current shunting capabilities by plating 82a and 82b with the plating being provided in thicknesses hereinbefore described. In this way, it is possible to achieve selective bending while still reducing the $I^2R$ heating which occurs in the distal extremity of the conductive element 81 to minimize heating of the soft plastic in the distal extremity of the flexible elongate tubular member 22. In such spaced-apart plating it should be appreciated that one or more of the portions 81a and 81b can be provided with tapered or stepped thicknesses of plating to achieve the desired curvatures in the bending.

In view of the foregoing it can be seen that there has been provided a device in which bends of different configurations can be readily placed in the distal extremity by selectively shunting of current around the conductive element to reduce $I^2R$ heating while at the same time achieving many different possible configurations for bends to be created in the distal extremity of the flexible elongate tubular member. Although the shunting of current has been achieved principally by the use of a highly conductive plating provided on the exterior surface of the conductive element, it should be appreciated that the shunting of current can be achieved in other ways, as for example by providing the conductive element in the form of a tubular member and plating the interior of the tubular member in appropriate locations in the desired thickness to achieve the desired shunting effects.

Although the present invention has been described in conjunction with the flexible distal extremity of the tip of a flexible elongate tubular member, it should be appreciated that the same construction and method can be utilized for a section of the flexible elongate tubular member remote from the distal extremity to form a bend or bends in that section. Also portions of the tubular member can be rigid, as for example in endoscopes.

What is claimed is:

1. A steerable catheter or guide wire device comprising an elongate tubular member having proximal and distal extremities and having a section with a plurality of lumens extending from the proximal extremity to the section, at least two conductive elements disposed in said lumens in said section of the elongate tubular member, at least one of said conductive elements being formed of a conductive metal alloy having a recoverable strain in excess of 1% and exhibiting a martensitic phase transformation, means coupled to the conductive elements for applying electrical current to at least one conductive element, said section having at least one portion and current conductive means carried by said at least one conductive element for shunting current flow around said at least one portion.

2. A device as in claim 1 wherein said current conductive means is in the form of a conductive material having a conductivity which is substantially greater than the conductivity of said at least one conductive element.

3. A device as in claim 2 wherein said current conductive means is in the form of a metallic plating adherent to and extending around the conductive element.

4. A device as in claim 3 wherein said plating is a noble metal.

5. A device as in claim 4 wherein said noble metal is selected from gold and silver.

6. A device as in claim 3 wherein said metallic plating has a portion thereof with a thickness ranging from 50 to 300 microinches.

7. A device as in claim 3 wherein said metallic plating is stepped to provided at least two steps in which one step has a thickness greater than the other step.

8. A device as in claim 3 wherein said metallic plating is tapered in thickness.

9. A device as in claim 8 wherein the taper of the metallic plating increases in thickness in a direction towards the proximal extremity of the at least one conductive element.

10. A device as in claim 3 wherein said plating is disposed in spaced-apart portions of the section of the at least one conductive element.

11. A device as in claim 1 wherein said section is at the distal extremity.

12. A device as in claim 11 wherein said section is flexible and wherein at least three circumferentially spaced-apart conductive elements are disposed in said lumens.

13. A flexible elongate steerable catheter or guide wire device comprising a flexible elongate tubular member having proximal and distal extremities and having a plurality of lumens extending therethrough from the proximal extremity to the distal extremity, at least three circumferentially spaced-apart conductive elements disposed in said lumens in the distal extremity of the flexible elongate tubular member, said conductive elements being formed of a conductive metal alloy having a recoverable strain in excess of 1% and which exhibits a martensitic phase transformation, means coupled to the conductive elements for selectively applying electrical current to the conductive elements and current conductive means carried by said conductive elements for shunting current flow around at least a portion of each of the conductive elements.

14. A device as in claim 13 wherein said current conductive means is in the form of a conductive material having a conductivity which is substantially greater than the conductivity of the conductive element.

15. A device as in claim 14 wherein said current conductive means is in the form of a plating adherent to and extending around the conductive element.

16. A device as in claim 15 wherein said plating is a noble metal.

17. A device as in claim 16 wherein said noble metal is selected from gold and silver.

18. A device as in claim 15 wherein said plating has a thickness ranging from 50 to 300 microinches.

19. A device as in claim 15 wherein said plating is stepped to provide at least two steps in which one step of the at least two steps has a thickness greater than the other step of the at least two steps.

20. A device as in claim 15 wherein said plating is tapered in thickness.

21. A device as in claim 20 wherein the taper of the plating increases in thickness in a direction towards the proximal extremity of the conductive element.

22. A device as in claim 15 wherein said plating is disposed on spaced-apart portions of the conductive element.

23. A method for reducing the $I^2R$ heating losses in the distal extremity of a flexible elongate tubular member used in a steerable catheter or guide wire and formed of a material and having a conductive element therein formed of a conductive metal alloy having recoverable strain in excess of 1% and exhibiting a martensitic phase transformation comprising the steps of passing an electrical current through the conductive element to cause heating of the same, and shunting the current around a predetermined portion of the conductive element to reduce the $I^2R$ heating of the conductive element to thereby reduce the transfer of heat to the material of the flexible elongate tubular member carrying the conductive element.

24. A method as in claim 23 wherein the shunting is carried out by providing a highly conductive path having a resistivity substantially less than that of the conductive element to reduce the $I^2R$ heating occurring by passage of current through the conductive element.

25. A method as in claim 23 wherein the shunting is carried out in progressively decreasing steps.

26. A method as in claim 23 wherein the shunting is carried out in a progressive substantially linear decrease in shunting.

27. A method as in claim 23 wherein the shunting is created at spaced-apart portions of the conductive element.

* * * * *